US012099001B2

(12) United States Patent
Olander et al.

(10) Patent No.: US 12,099,001 B2
(45) Date of Patent: Sep. 24, 2024

(54) SYSTEMS AND METHODS FOR MONITORING BALE COMPOSITION

(71) Applicant: Great Plains Manufacturing, Inc., Salina, KS (US)

(72) Inventors: Brian Olander, Salina, KS (US); Taylor Bozarth, Lindsborg, KS (US); James Edward Schott, McPherson, KS (US)

(73) Assignee: Great Plains Manufacturing, Inc., Salina, KS (US)

( * ) Notice: Subject to any disclaimer, the term of this patent is extended or adjusted under 35 U.S.C. 154(b) by 1009 days.

(21) Appl. No.: 17/076,285

(22) Filed: Oct. 21, 2020

(65) Prior Publication Data

US 2021/0116361 A1    Apr. 22, 2021

Related U.S. Application Data

(60) Provisional application No. 62/924,461, filed on Oct. 22, 2019, provisional application No. 62/924,446, filed on Oct. 22, 2019.

(51) Int. Cl.
*G01N 21/31* (2006.01)
*A01F 15/04* (2006.01)
(Continued)

(52) U.S. Cl.
CPC .............. *G01N 21/31* (2013.01); *A01F 15/04* (2013.01); *B30B 9/30* (2013.01); *G01N 21/55* (2013.01); *G01N 33/0098* (2013.01); *G06T 7/0002* (2013.01); *A01F 15/0715* (2013.01); *A01F 2015/0808* (2013.01); *A01F 15/148* (2013.01);
(Continued)

(58) Field of Classification Search
CPC .. G01N 2033/245; A01B 79/005; B30B 9/30; A01F 15/0715; A01F 2015/076
See application file for complete search history.

(56) References Cited

U.S. PATENT DOCUMENTS 6,431,981 B1    8/2002  Shinners et al.
7,415,924 B2    8/2008  Roberts
(Continued)

FOREIGN PATENT DOCUMENTS

WO        2007/050192 A2    5/2007

OTHER PUBLICATIONS

Ahmed Kayad, "Assessing the Spatio-Temporal Alfalfa Yield Variability Using Landsat-8 and Yield Monitor Data at Field Scale", 2018 (Year: 2018).*
(Continued)

*Primary Examiner* — Maurice C Smith
(74) *Attorney, Agent, or Firm* — Hovey Williams LLP; Kameron D. Kelly (57) ABSTRACT

A bale composition determination system comprising a baler configured to pick up crop material cut and lying on the ground in the form of a windrow and to form bales of the crop material. The system additionally includes one or more sensors configured to obtain electromagnetic reflectance information for the crop material. The system further includes a control system configured to receive the electromagnetic reflectance information for the crop material and to generate vegetation index values for the bales of crop material based on the electromagnetic reflectance information.

24 Claims, 3 Drawing Sheets

(51) Int. Cl.
   *B30B 9/30*      (2006.01)
   *G01N 21/55*     (2014.01)
   *G01N 33/00*     (2006.01)
   *G06T 7/00*      (2017.01)
   *A01F 15/07*     (2006.01)
   *A01F 15/08*     (2006.01)
   *A01F 15/14*     (2006.01)
   *G06K 19/07*     (2006.01)

(52) U.S. Cl.
   CPC .............. *G06K 19/0723* (2013.01); *G06T 2207/10036* (2013.01)

(56) References Cited

U.S. PATENT DOCUMENTS

| | | | |
|---|---|---|---|
| 7,725,233 B2 | 5/2010 | Hendrickson et al. | |
| 9,560,808 B2* | 2/2017 | Foster | A01F 15/08 |
| 9,632,070 B2 | 4/2017 | Roberts | |
| 9,986,690 B2 | 6/2018 | Younk et al. | |
| 10,149,422 B2 | 12/2018 | Tippery et al. | |
| 10,276,015 B2 | 4/2019 | Lang et al. | |
| 2018/0084730 A1 | 3/2018 | Younk et al. | |
| 2018/0299327 A1* | 10/2018 | Zhao | A01C 21/007 |

OTHER PUBLICATIONS

Humble Haymakers, "John Deere 348 Square Baler—Baling 1st Cut Timothy Hay", https://www.youtube.com/watch?v=upPH15TbPy0 2016 (Year: 2016).*

Ahmed Kayad, "Performance Evaluation of Hay Yield Monitoring System in Large Rectangular Baler", 2015 (Year: 2015).*

Sohaib K. M. Abujayyab, "Automated Prediction System for Vegetation Cover Based On Modis—NDVI Satellite Data and Neural Networks", Nov. 14-15, 2019 (Year: 2019).*

European Examination Report dated Mar. 10, 2023 for related European Application No. 20203413.8, 6 pages.

* cited by examiner

SYSTEMS AND METHODS FOR MONITORING BALE COMPOSITION

RELATED APPLICATION

The present non-provisional patent application claims priority benefit to prior-filed U.S. Provisional Patent Application Ser. No. 62/924,446, filed on Oct. 22, 2019, and entitled "BALE QUALITY DETERMINATION SYSTEM," and to prior-filed U.S. Provisional Patent Application Ser. No. 62/924,461, filed on Oct. 22, 2019, and entitled "KNOTTER MISTIE DETECTION SYSTEM." The entireties of both above-identified, prior-filed provisional patent applications are hereby incorporated by reference into the present non-provisional patent application.

FIELD OF THE INVENTION

Embodiments of the present invention are generally directed to systems and methods for determining and improving bale quality. The quality of a bale of crop material may be based, at least in part, on the composition of the bale as well as on the propriety of the knots of securement lines tied around the bale.

BACKGROUND OF THE INVENTION

To produce bales of crop material, a prime mover such as a tractor will generally propel a baling implement (referred to herein as a "baler") through a field of crop material that has been cut and is lying in the field in windrows. The baler is configured to pick up the crop material and stuff the crop material into a baling chamber where the crop material is compressed into bales via a plunger. A knotting system will tie one or more securement lines (e.g., twine) around each bale to hold the bale together before the bale is ejected from the baler. If the knotting system fails to properly tie securement lines around the bale, the bale will fall apart and will not be usable. Currently, there does not exist any systems or methods for detecting when misties occur for balers that make small, square bales of crop material.

In addition, when producing bales of crop material, such as hay for animal food, it is useful to obtain metrics to identify the quality of the crop material (e.g., alfalfa or grass) in an individual bale or groups of bales. Such metrics may be used to approximate a relative feed value (RFV) for the bales. However, RFV information only provides a partial picture of the quality of that hay. Furthermore, it would be beneficial if such metrics could be obtained in real-time so that an operator of the baler can quickly make necessary adjustments to the bale-forming process to improve bale quality.

SUMMARY OF THE INVENTION

In one embodiment of the present invention, there is provided a bale composition determination system comprising a baler configured to pick up crop material cut and lying on the ground in the form of a windrow and to form bales of the crop material. The system additionally includes one or more sensors configured to obtain electromagnetic reflectance information for the crop material. The system further includes a control system configured to receive the electromagnetic reflectance information for the crop material and to generate vegetation index values for the bales of crop material based on the electromagnetic reflectance information.

In another embodiment of the present invention, there is provided a bale composition determination system for bales of crop material formed by a baler. The baler is configured to pick up the crop material having been cut and lying on the ground in the form of a windrow. The system comprises one or more sensor configured to obtain electromagnetic reflectance information for the crop material. The system further includes a computing device configured to receive the electromagnetic reflectance information for the crop material and to generate vegetation index values for the bales of crop material based on the electromagnetic reflectance information.

In another embodiment of the present invention, there is provided a method for determining bale composition. The method comprises the step of picking up crop material cut and lying on the ground in the form of a windrow. An additional step includes forming the crop material into bales. An additional step includes obtaining electromagnetic reflectance information for the crop material. A further step includes generating vegetation index values for the bales of crop material based on the electromagnetic reflectance information.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the present invention will be apparent from the following detailed description of the embodiments and the accompanying drawing figures.

BRIEF DESCRIPTION OF THE FIGURES

Embodiments of the present invention are described herein with reference to the following drawing figures, wherein.

The drawing figures do not limit the present invention to the specific embodiments disclosed and described herein. The drawings are not necessarily to scale, emphasis instead being placed upon clearly illustrating the principles of the invention.

DETAILED DESCRIPTION

The following detailed description of the present invention references various embodiments. The embodiments are intended to describe aspects of the invention in sufficient detail to enable those skilled in the art to practice the invention. Other embodiments can be utilized and changes can be made without departing from the scope of the present invention. The following detailed description is, therefore, not to be taken in a limiting sense. The scope of the present invention is defined only by the appended claims, along with the full scope of equivalents to which such claims are entitled.

Figure 1:
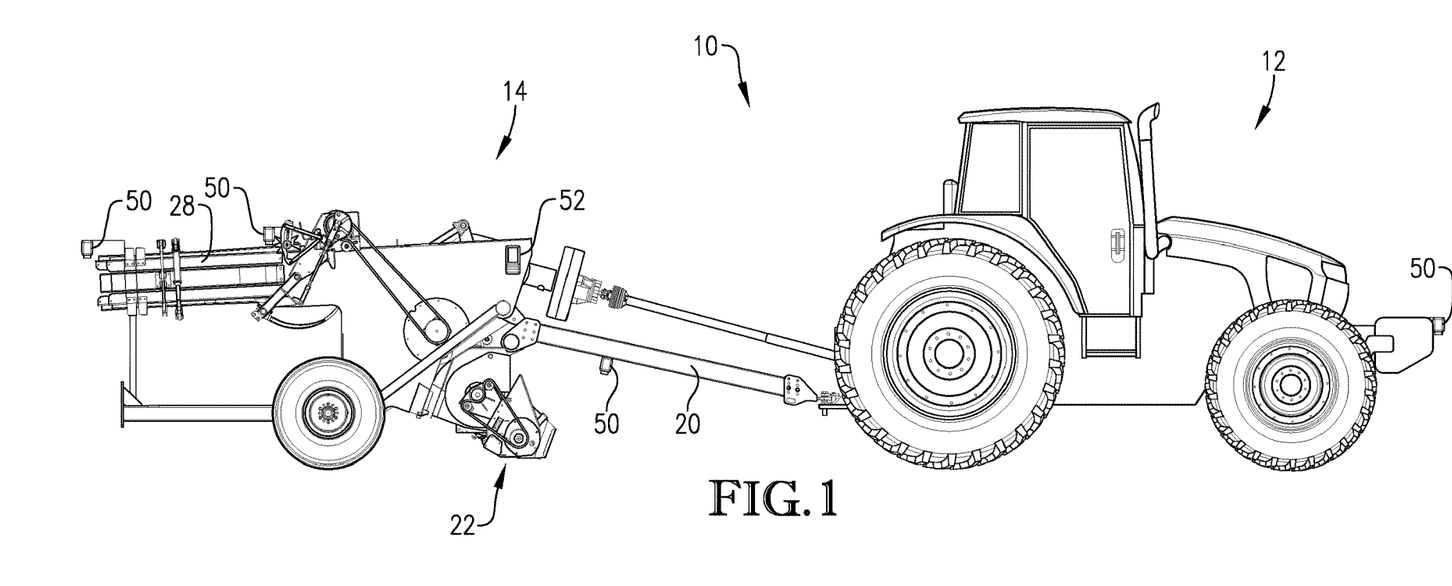
FIG. 1 is a side elevation view of a bale quality system in the form of a bale composition monitoring system incorporated with a tractor and a baler according to embodiments of the present invention.

Broadly, embodiments of the present invention are directed to systems and methods for monitoring and improving bale quality. As illustrated in FIG. 1, a bale quality system 10 according to the present invention may comprise a prime mover, such as tractor 12, and a baler 14 that is connected to the tractor 12, such that the tractor 12 can propel the baler 14 through a field. The field may have crop material that has previously been cut and arranged on the surface of the field in windrows. As such, the baler 14 can pass over the windrows to collect the crop material and form bales therefrom. The bale quality system 10 may, in some embodiments, comprise a knotter mistie detection system configured to determine whether or not securement lines have been properly tied around the bales being formed by the baler 14. Alternatively, or in addition, the bale quality system 10 may, in some embodiments, comprise a bale composition monitoring system configured to monitor a composition of the crop material from which the bales are formed by the baler 14.

Figure 2:
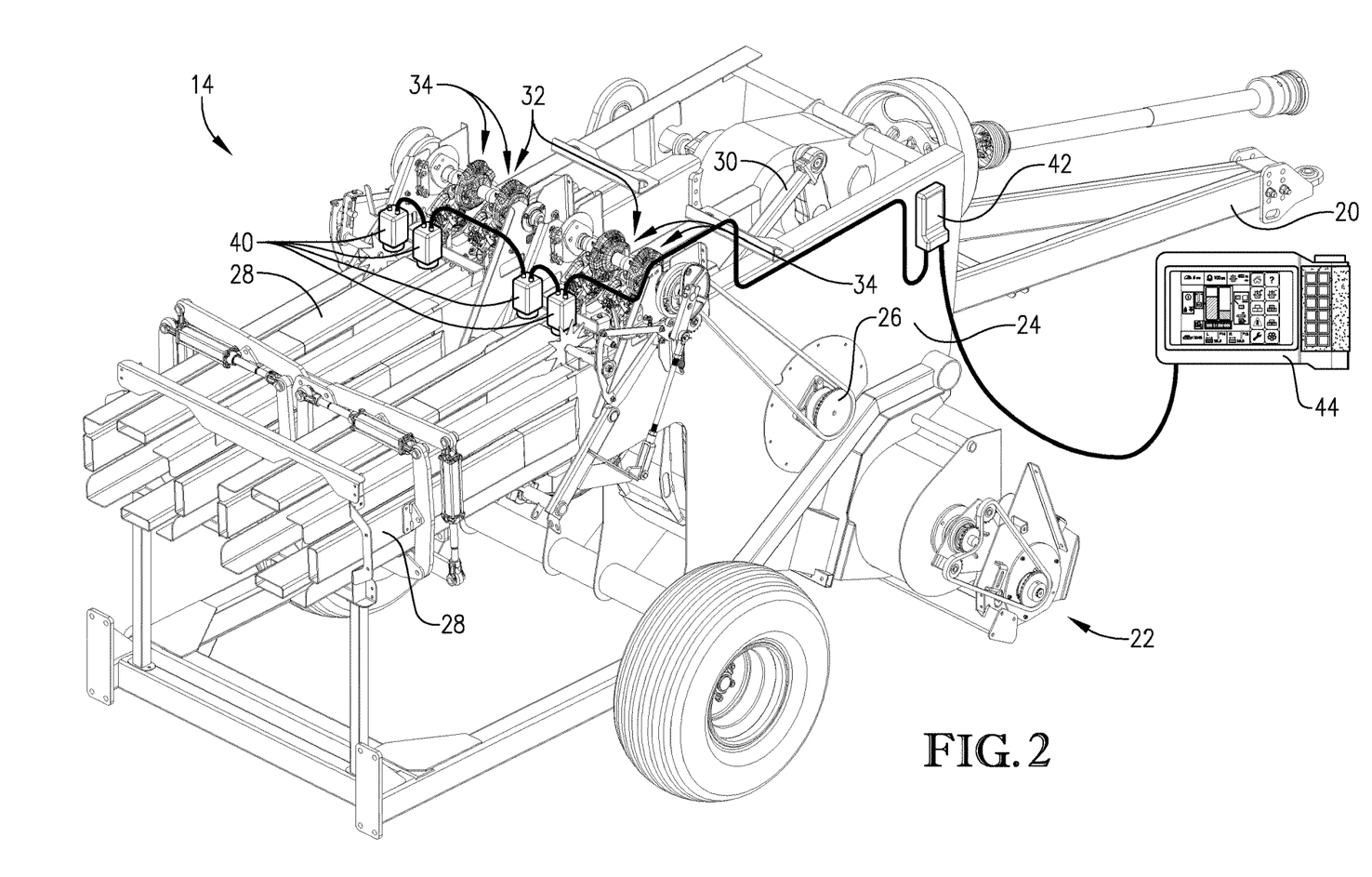
FIG. 2 is a rear perspective view of the baler from FIG. 1 including a bale quality system in the form of a knotter mistie detection system.

Turning to the baler 14 in more detail, as shown in FIG. 2, the baler 14 may, in some embodiments, be configured as a square baler that forms small, square bales of crop material. It should be understood, however, that the term "square baler" is used in its conventional sense to denote a baler that forms bales having the general shape of cuboid. In more detail, small, square bales will be formed having a length of between thirty-two and forty-eight, although commonly about thirty-six inches. In addition, the width of such small, square bales will be about eighteen inches, and the height of such small, square bales will be about fourteen inches. Although the present disclosure is primarily related to monitoring and improving the bale quality for small, square bales (e.g., cuboid shaped bales), it is contemplated that some embodiments of the present invention may be used to monitor and improve bale quality for other types and sizes of bales.

Returning to FIG. 2, the baler 14 may comprise a tow bar 20 configured to connect with the tractor 12, such that the tractor 12 can pull the baler 14 through the field. During such transport, the baler 14 may pick up crop material laying on the surface of the field in a windrow via a pickup assembly 22. The pickup assembly 22 may comprise a rotor or auger configured to pick up crop material and direct the crop material upward and rearward to a pre-compression chamber 24. In the pre-compression chamber 24, a stuffer assembly 26 may force charges of the crop material upward into one or more baling chambers 28. The baler 14 may further comprise one or more plungers 30 for compressing the charges of crop material within the baling chambers 28 into bales. Once a bale has been formed to an appropriate size, the baler 14 may include one or more knotter assemblies 32 configured to tie securement lines (e.g., twine) around the bale to hold the bale together.

As shown in FIG. 2, the baler 14 may comprise two baling chambers 28 for simultaneously forming bales in each of the baling chambers 28. However, the baler 14 may comprise various other numbers of baling chambers 28, such as one, three, four, or more baling chambers 28. In general, the baler 14 will include a number of plungers 30 that corresponds with the number of baling chambers 28. For instance, with the embodiment shown in FIG. 2, the baler 14 may comprise two plungers 30, with each plunger 30 configured to compress charges of crop material into a bale in one of the baling chambers 28. Similarly, the baler 14 will generally include a number of knotter assemblies 32 that corresponds with the number of baling chambers 28. For instance, with the embodiment shown in FIG. 2, the baler 14 may comprise two knotter assemblies 32, with each knotter assembly 32 configured to tie securement lines around the bales being formed in one of the baling chambers 28. In some embodiments, each knotter assembly 32 may comprise two or more knotting mechanisms 34 each being configured to tie a single securement line around a bale. For example, as shown in FIG. 2, each knotter assembly 32 may be configured to include two knotting mechanisms 34 so as to tie two securement lines around each bale.

Each knotting mechanism 34 may comprise: a knotter disc, a billhook assembly (e.g., a billhook, a billhook spring, a billhook cam, a billhook pinion), strand holder, strand knife, and/or the like. Furthermore, each knotter assembly 32 may include a rotatable shaft, which may be configured as an axle, and which is configured actuate various of the components of the associated knotting mechanisms 34. As such, in the embodiments that include two knotter assemblies 32, a left-side knotter assembly 32 may include one rotatable shaft, and a right-side knotter assembly 32 may include one rotatable shaft. In addition, each of the knotter assemblies 32 may include one or more needles used to wrap a securement line completely around a bale of crop material once the bale is fully formed, such that the associated knotting mechanism 34 can tie the securement line securely around the fully formed bale. As was noted above, each knotter assembly 32 may include a plurality of knotting mechanisms and a corresponding plurality of needles, such that each knotter assembly 32 can be configured to wrap and tie a plurality of (e.g., two) securement lines around a bale being formed in a baling chamber 28. Each knotter assembly 32 may additionally comprise a trip mechanism that can be used to initiate the tying process once a bale of crop material has been fully formed.

Figure 3:
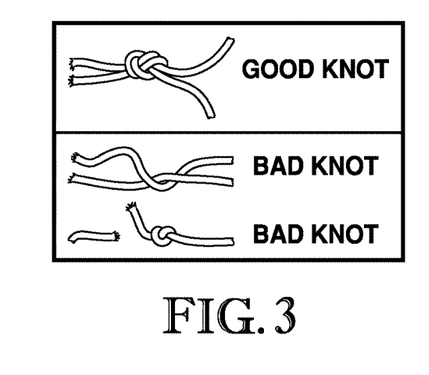
FIG. 3 is a representation of knot templates, including good knots and bad knots.

As was discussed previously, it can be problematic if misties occur when tying securement lines around the bales. Such misties can cause the bale to fall apart, rendering them unusable. FIG. 3 illustrates exemplary differences between "good knots" in which the securement lines are properly tied together and "bad knots" in which a mistie has occurred leaving the securement lines not properly tied together. As shown, a bad knot or a mistie might occur if the knotting mechanism fails to properly/completely tie a securement line into a knot and/or if the securement line breaks or is cut.

To detect if a mistie has occurred, bale quality system 10 may comprise a knotter mistie detection system including one or more image sensors 40, a control system 42, and a graphic display 44, as illustrated in FIG. 2. In some embodiments, the image sensors 40 may comprise digital cameras configured to obtain data in the form of photographs (e.g., still images data and/or video data). The cameras may comprise an optical system having lens focus light onto an electronic light sensors (e.g., a charge coupled device (CCD) or complimentary metal oxide semiconductor (CMOS)) to create digital images and/or videos. In some embodiments, the cameras may be associated with processing elements and/or memory elements. As such, the cameras may, at least temporarily, store and delete images and/or videos from internal memory elements.

Regardless, the data comprising the images and/or videos obtained from the image sensors 40 may be transmitted to the control system 42 for processing, and particularly to determine if a mistie of a securement line has occurred, as will be described in more detail below. If the control system 42 determines that a mistie has occurred (sometimes referred to herein as a "mistie event"), the control system 42 may transmit an indication of such a mistie to the graphic display 44 so as to alert the operator of the baler 14.

Figure 4:
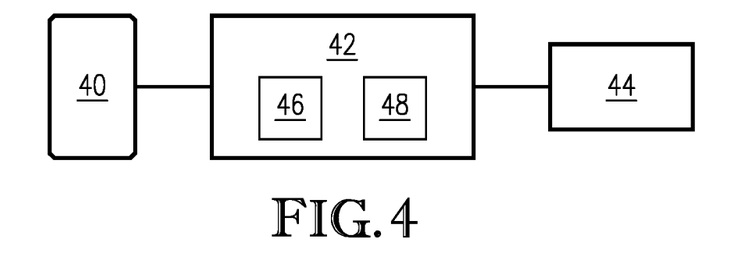
FIG. 4 is a schematic illustration of the knotter mistie detection system from FIG. 2.

In more detail, the control system 42 may comprise a computing device with, as illustrated in FIG. 4, one or more processing elements 46 and/or one or more memory elements 48. The memory elements 48 may store a computer program, which when executed by the processing elements 46, functions to perform the various operations discussed herein. In more detail, the processing elements 46 may comprise processors, microprocessors (single-core and multi-core), microcontrollers, DSPs, field-programmable gate arrays (FPGAs), analog and/or digital application-specific integrated circuits (ASICs), or the like, or combinations thereof. The processing elements 46 may generally execute, process, or run instructions, code, code segments, software, firmware, programs, applications, apps, processes, services, daemons, or the like. The processing elements 46 may also include hardware components such as finite-state machines, sequential and combinational logic, and other electronic circuits that can perform the functions necessary for the operation of the present invention. The processing elements 46 may be in communication with other electronic components through serial or parallel links that include address busses, data busses, control lines, and the like.

The memory elements 48 may comprise data storage components, such as read-only memory (ROM), programmable ROM, erasable programmable ROM, random-access memory (RAM) such as static RAM (SRAM) or dynamic RAM (DRAM), cache memory, hard disks, floppy disks, optical disks, flash memory, thumb drives, universal serial bus (USB) drives, or the like, or combinations thereof. In some embodiments, the memory elements 48 may be embedded in, or packaged in the same package as, the processing elements 46. The memory elements 48 may include, or may constitute, a non-transitory "computer-readable medium." The memory elements 48 may store the instructions, code, code segments, software, firmware, programs, applications, apps, services, daemons, or the like that are executed by the processing elements 46. In particular, as will be described in more detail below, the memory elements 48 may store images and/or videos of knot templates (e.g., both good knots and bad knots) such that embodiments of the present invention can determine if a mistie has occurred. The memory elements 48 may also be able to store all the images and/or videos obtained by the image sensors 40.

The graphic display 44 may comprise an electronic display, such as a cathode ray tube, liquid crystal display, plasma, or touchscreen display that is operable to display visual graphics, images, text, etc. In certain embodiments, the computer program of the present invention facilitates interaction and communication through a graphical user interface (GUI) which can be presented on the graphic display 44. The GUI may enable the user to interact with the graphic display 44 by viewing, as well as by touching or pointing at display areas to provide information to the control system.

As will be discussed in more detail below and as shown in FIG. 2, the image sensors 40 may be positioned on, in, or adjacent to the baling chambers 28 so as to be able to obtain images and/or video of the securement lines being tied (or having been tied) around the bales. The control system 42 may be positioned on, in, or adjacent to the baler 14 and/or the tractor 12. In some embodiments, the control system 42 may be positioned inside an operator cab of the tractor.

Similarly, the graphic display 44 may be positioned on, in, or adjacent to the baler 14 and/or the tractor 12. In some embodiments, the graphic display 44 may be positioned inside an operator cab of the tractor 12. For example the graphic display 44 may be positioned in an operator cab of the tractor 12, such that the graphic display 44 is within eye view of the operator to permit the operator to easily view the graphic display 44 and the GUI presented thereon as the operator is controlling the tractor 12 and the baler 14 to form bales of crop material. As shown in FIG. 2, each of the image sensors 40, the control system 42, and the graphic display 44 may be communicably coupled with each other (e.g., via wires or cables) so as to be configured to transmit information and data back and forth between each other. In some other embodiments, however, the image sensors 40, control system 42, and graphic display 44 may be configured to communicate and transmit data to each other wirelessly (e.g., via Bluetooth, WiFi, cellular, etc.). As such, in some further alternatives, the control system 42 may be remotely located from the baler 14 and tractor 12. In such embodiments, the control system 42 may provide remote processing/analyzing capabilities (e.g., via processing elements 46) and data storage (e.g., via memory elements 48), such as via a distributed or non-centralized database (e.g., in the cloud). Similarly, the graphic display 44 may, in some embodiments, be positioned remotely from the tractor 14 and baler 12.

Remaining with FIG. 2, the image sensors 40 may, in some embodiments, be positioned adjacent to the knotter assemblies 32 and/or adjacent to the baling chambers 28. Because the image sensors 40 are configured to obtain images or videos of knots of the securement lines being tied around the bales (so as to determine if a mistie event has occurred), some embodiments provide for at least one image sensor 40 to be associated with each knotting mechanism 34 of the knotter assemblies 32. Thus, for example, the baler 14 shown in the figures includes two baling chambers 28 each being associated with a knotter assembly 32. Furthermore, each knotter assembly 32 includes two knotting mechanisms 34 (so as to wrap and tie two securement lines around each bale). As a result, the system 10 may include four image sensors 40, with each image sensor 40 being configured to obtain images and/or video of a given securement line being wrapped and tied around a bale. Thus, the baler 14 may include a pair of image sensors 40 for monitoring each pair of securement lines being secured around each bale, and particularly for monitoring each pair of knots of securement lines being secured around each bale. Regardless, embodiments provide for the system 10 to include more or less than four image sensors 40.

In some embodiments, each of the image sensors 40 may be directed or aimed towards one of the knotting mechanisms 34 of the knotter assemblies 32, so as to be configured to obtain images and/or video of a securement line being tied around a bale being tied by the associated knotting mechanism 34. Specifically, the image sensors 40 may be used to observe whether knots of securement lines are being tied properly (i.e., good knots) around the bales by taking images or a video of each knotting cycle performed by the knotting mechanisms 34. Such images or video may be representative of a complete knot tying process taking place during a knotting cycle. For example, the image sensors 40 may be configured to obtain images or videos through the complete knot tying processes performed by each the knotting mechanisms 34 of the knotter assemblies 32 (e.g., to observe whether each knot came off of the billhook correctly and/or to see whether each knot is properly formed on the respective bale).

Alternatively, or in addition, each of the image sensors 40 may be positioned on or adjacent a top side of an associated bailing chamber 28 (or inside the baling chamber 28) and directed or aimed towards an interior of the associated baling chamber 28 at a location adjacent to or downstream of a location at which a bale is being tied with securement line by the knotting mechanisms 34. As such, the image sensors 40 will be configured to obtain images and/or video of a securement lines being (or having been) tied around bales as the bales travel through the baling chambers 28. In further alternatives, or additionally, each of the image sensors 40 may be directed or aimed towards a dispensing end of an associated baling chamber 28 (i.e., free ends of the baling chambers 28 *e* shown on the left side of FIG. 2). As such, each of the image sensors 40 will be configured to obtain mages and/or video of a securement line wrapped and tied around a bale as the bale is being ejected from the baler 14 and/or as the bale is deposited on the surface of the field. Regardless, the image sensors 40 may be configured to obtain images or videos of the securement lines on the bales, and particularly of the knots formed with the securement lines, as the bales travel through or are ejected from the baling chambers 28. As such, the image sensors 40 may be configured to observe whether the knots are properly tied and held together on the bales after several plunger 30 strokes have occurred subsequent to the knots being tied. Alternatively, the image sensors 40 may be configured to observe whether the knots are properly held together on the bale as (or after) the bales are ejected from the baling chamber 28 and deposited onto the surface of the field.

In some embodiments, a plurality of image sensors 40 may be used to obtain images and/or video at each of such above-described locations (e.g., the image sensors 40 may be directed or aimed at each of (i) the knotter assemblies 32, (ii) the interior of the baling chambers 28, and/or (ii) the dispensing ends of the baling chambers 28. Thus, the image sensors 40 may be used to simultaneously observe whether each knot came off of the billhook correctly, whether each knot is properly formed on the respective bale, whether each knot remains properly tied and held together on the bale after several plunger 30 strokes occurs subsequent to the knot being tied, and/or whether each knot remains properly tied on the bale as the bale is ejected from the baling chamber 28. In some embodiments, the image sensors 40 may only capture images and/or video of the securement lines periodically, such as after the knotter assemblies 32 complete a knot-tying cycle/process. In other embodiments, the image sensors 40 may continuously capture images and/or video of the securement lines tied on the bales as the bales are formed in, travel through, and are ejected from the baling chambers 28.

In some embodiments, the image sensors 40 may be configured with motion capabilities so as to be capable of following the motion of objects (e.g., the motion of the knotting mechanisms 34 and/or of the bales themselves) as such objects move or actuate during the bale-forming process (including the knot-tying process). Thus, the image sensors 40 may continually track and follow (so as to continuously obtain image and/or video) (i) the knotter assemblies 32 tying knots of securement lines around the bales, (ii) the bales (and the knots tied thereon) as the bales are being formed within the baling chamber 28, and (iii) the bales (and the knots tied thereon) as the bales are dispensed from the baling chamber 28 and/or deposited on the surface of the field.

Once the images and/or video of the knots of securement lines tied (or mistied) around the bales are obtained via the image sensors 40, such images and/or video may be transmitted to the control system 42 for analysis and/or processing to determine if a mistie has occurred. Specifically, the control system 42 may process the images and/or video through image-recognition routines (that may form part of the computer program/software stored on the memory elements 48) to analyze the images and/or video, such as perhaps extracting data from the images and/or video that can be used to determine if a mistie has occurred. If a mistie is determined to have occurred, an alert may be generated and transmitted to the graphic display 44 to alert the operator of the baler 14 that a mistie has occurred. As was described previously, the control system 42 may be coupled and/or associated with the baler 14 or the tractor 12. As such, the analysis and/or processing of the images and/or video may be performed locally at the baler 14 or tractor 12. Alternatively, the control system 42 may be separated from the baler 14 and/or tractor 12, such that the analysis and/or processing of the images and/or video may be performed remotely from the baler 14 or tractor 12 (e.g., in the cloud).

For example, as described previously, embodiments of the present invention may include a control system 42 which may be in the form of and/or include a computing device with processing elements 46 and memory elements 48 (e.g., as perhaps providing access to a database). The control system 42 may store knot template data that is associated with good knots and bad knots (it being understood that bad knots are associated with misties of securement lines). The knot template data may comprise images and/or videos of bad knots and good knots (referred to herein as "knot templates"), such as those illustrated in FIG. 3. Furthermore, the control system 42 can compare the images and/or video of knots of securement lines tied (or mistied) around bales as obtained by the image sensors 40 with the knot templates to determine if a mistie has occurred. Specifically, the control system 42 may execute image-recognition software to compare the images and/or video obtained by the image sensors 40 with the knot templates to determine if the images and/or video obtained by the image sensors 40 are sufficiently similar to and/or match stored images and/or video of good knot templates (See, e.g., FIG. 3). If sufficiently similar, the control system 42 will determine that image sensors 40 have detected good knots being tied around the bales. Similarly, the control system 42 may execute image-recognition software to compare images and/or video obtained by the image sensors 40 with the knot templates to determine if the images and/or video are sufficiently similar to and/or match stored images and/or video of bad knot templates (See, e.g., FIG. 3). If sufficiently similar, the control system 42 will determine that the image sensors 40 have detected bad knots (or misties/mistie events) being tied around the bales. Embodiments may also implement machine learning techniques to improve the efficiency and accuracy of determining good knots and mistie events.

If a mistie has occurred, embodiments may provide for a notification of such a mistie event to be provided to an operator of the baler 10. Specifically, the control system 42 may transmit information indicative of a mistie to the graphic display 44, such that the graphic display 44 can provide a graphic/visual indication of such a mistie to the operator of the baler 14. As was discussed previously, the graphic display 44 may be positioned within the operator cab of the tractor 12 pulling the baler 14, such that the operator can be informed of the mistie while operating the baler 14 without leaving the cab of the tractor 12. In other embodiments, the graphic display 44 may include or be associated with a speaker such that an audible alert may also be provided to the operator in the case of a mistie. Some embodiments of the present invention may also be configured to indicate to the operator a reason why a particular mistie occurred. For example, each of the image and/or video templates of bad knots may also be associated with data in the form of the potential reason for obtaining such a bad knot. Such reasons may be, for example, (i) an improper tying process by the knotting mechanism 34, (ii) a broken component of the knotting mechanism 34, (iii) a foreign object interfering with the tying process, (iv) the securement line becoming cut or broken, (v) or the like.

Figure 5:
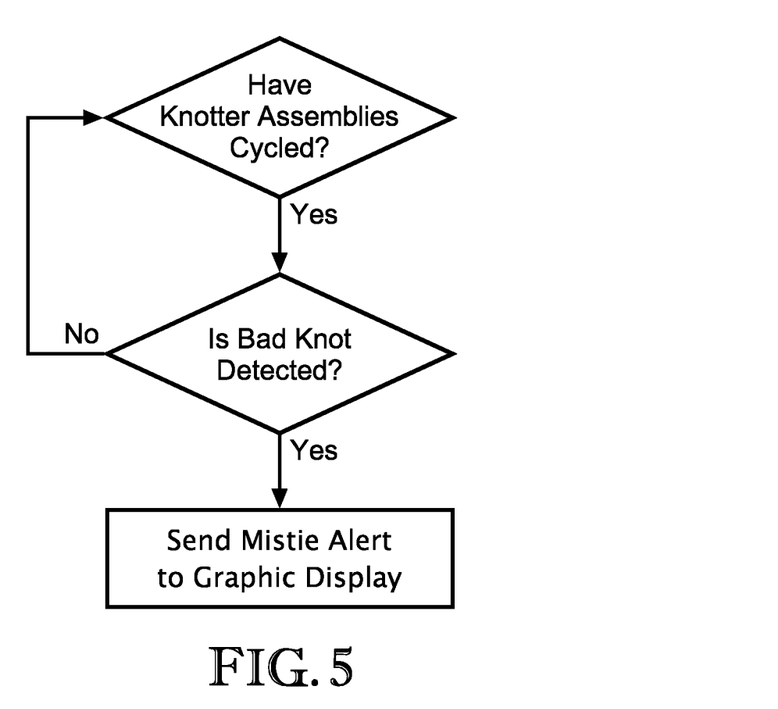
FIG. 5 is a flowchart illustrating a process for detecting knot misties according to embodiments of the present invention.

An exemplary flow chart for determining bale quality, and particularly for identifying misties, is shown in FIG. 5. As previously described, the system 10 may include one or more image sensors 40 positioned on the baler 14 configured to obtain images and/or video of the knots of securement lines on the bales being formed in the baler. The system 10 may also include one or more other sensors configured to determine whether the knotter assemblies 32 have cycled to perform a knot-tying process on one or more bales. If the sensors determine that a knotter assembly 32 has cycled to tie a knot on a bale, the image sensors 40 may observe the knot on the bale (e.g., may obtain an image and/or video of the knot). The image and/or video of the knot may be transmitted to the control system 42 for analysis. Specifically, the control system 42 may compare the image and/or video of the knot with knot templates of good and/or bad knots. If, based on the comparison, the control system 42 determines that the knot formed on the bale is a bad knot (e.g., not tied, improperly tied, or broken material), then an alert signal may be sent to the operator of the baler (e.g., to the graphical display 44 positioned within a cab of the tractor). The operator may then stop the baler 14 to correct the issue that caused the mistie, which may include performing maintenance on the baler 14. In some other embodiments, the system 10 may transmit an alert to a remote location, such as to a remote computing device (e.g., a mobile device of the operator). As was described previously, the control system 42 may be coupled and/or associated with the baler 14 or the tractor 12. As such, the knot templates and the images and/or video obtained by the image sensors 40 may be stored (e.g., for future use, analysis, and/or processing) locally at the baler 14 or tractor 12. Alternatively, the control system 42 may be separated from the baler 14 and/or tractor 12, such that the a knot templates and the images and/or video obtained by the image sensors 40 may be stored (e.g., for future use, analysis, and/or processing) remotely from the baler 14 or tractor 12 (e.g., in the cloud).

In view of the above, embodiments of the present invention may provide a method for identifying misties of a securement line around a bale of crop material being formed in a baler 14. The method may comprise a step of picking up crop material from a windrow. An additional step may include forming the crop material into bales. During the forming of the bales of crop material, one or more securement lines are tied around each bale. An additional step includes obtaining, via one or more image sensor 40, images or video of the securement lines. The image sensor may be configured to monitor one or more of the knotter assemblies 32, the securement lines, and the bales. In some embodiments, the image sensors 40 are positioned on or adjacent a top side of the baling chambers 28 of the baler 14. As such, the image sensors 40 may be aimed towards the knotter assemblies 32 and configured to obtain images or video of the knotter assemblies 32 tying knots of securement lines around the bales. Thus, the control system 42 is configured to determine if a mistie event has occurred by analyzing the images or videos of the knotter assemblies 32 tying knots of the securement lines around the bales. In other embodiments, the image sensors 40 are aimed towards an interior of the baling chambers 28 and are configured to obtain images or video of knots of securement lines having been tied around the bales. Thus, the control system 42 is configured to determine if a mistie event has occurred by analyzing the images or videos of the knots of the securement lines tied around the bales. In other embodiments, the image sensors 40 are aimed towards an outlet of the baling chambers 28 and are configured to obtain images or video of knots of securement lines having been tied around the bales. Thus, the control system 42 is configured to determine if a mistie event has occurred by analyzing the images or videos of the knots of the securement lines tied around the bales. An additional step includes determining via the images and/or video whether a mistie event has occurred for at least one of the securement lines (e.g., by comparing the images and/or video with knot templates). A further step includes providing an indication that a mistie event has occurred, via a graphic display 44, to an operator of a baler 14.

Figure 6:
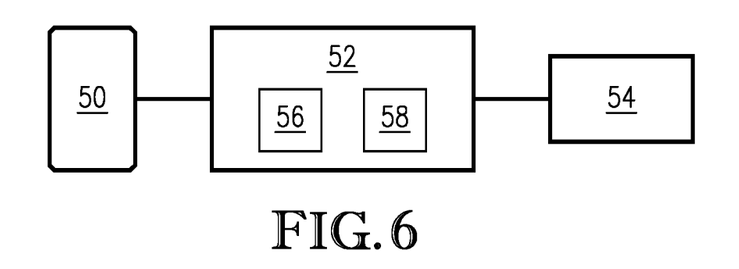
FIG. 6 is a schematic illustration of the bale composition monitoring system from FIG. 1.

Alternatively, or in addition to determining whether a mistie event occurs, the bale quality system 10 may comprise a bale composition monitoring system configured to monitor and/or detect the composition and/or content of crop material being formed into bales by the baler 14. As illustrated in FIG. 6, the bale quality system may comprise one or more sensors 50, a control system 52, and a graphic display 54. In some embodiments, the sensors 50 may comprise sensors configured to detect electromagnetic (EM) spectrum reflectance data (e.g., multi-spectrum EM reflectance intensity), for crop material (e.g., alfalfa or grass) contained in (or that is to be contained in) a bale. Once obtained by the sensors 50, such EM reflectance data may be transmitted to the control system 52, which is configured to analyze and/or process the EM spectrum reflectance data and to record such data in association with each bale or groups of bales being formed by the baler 14. The graphic display 54 may, as discussed in more detail, be configured to present the EM spectrum reflectance data and/or associated alerts to the operator of the baler 14

In some embodiments, the sensors 50 may comprise multi-spectrum EM sensors, cameras, and/or light sensors, such as Red-Green-Blue (RGB) sensors configured to obtain RGB EM reflectance data. Alternatively, the sensors 50 may comprise infrared, near-infrared, or other wavelength sensors configured to obtain infrared, near-infrared or other wavelength EM reflectance data. Regardless, the sensors 50 may comprise electronic light sensors (e.g., a charge coupled device (CCD) or complimentary metal oxide semiconductor (CMOS)) configured to obtain EM reflectance data. As such, the EM reflectance data obtained by the sensors 50 and/or recorded by the control system 52 may be RGB data values from the visible portion of the electromagnetic spectrum, or multi-spectrum imaging data that includes the infrared, near-infrared, or other portions of the EM spectrum.

It should be understood that the control system 52 may be similar to (or the same as) the control system 42 previously described. For instance, as illustrated in FIG. 6, the control system 52 may include one or more processing elements 56 and/or one or more memory elements 58 similar to (or the same as) the processing elements 46 and memory elements 48 of the control system 42 previously described. The control system 52 may store and execute a computer program/software to perform the various functions described herein. Furthermore, the control system 52 may be coupled or associated with the baler 14 or the tractor 12. In further alternatives, the control system 52 may be remotely located from the baler 14 and tractor 12. In such embodiments, the control system 52 may provide remote processing/analyzing capabilities (e.g., via processing elements 56) and data storage (e.g., via memory elements 58), such as via a distributed or non-centralized database (e.g., in the cloud). Similarly, the graphic display 54 may be similar to (or the same as) the graphic display 44 previously described. For example, the graphic display 54 may be positioned within an operator cab of the tractor 12. Alternatively, the graphic display 54 may be coupled or associated with the baler 14, or may be positioned remotely from the tractor 14 and baler 12. Each of the sensors 50, the control system 52, and/or the graphic display 54 may be communicably coupled via wired or wireless communication (e.g., via Bluetooth, WiFi, cellular, etc.). As such, the EM reflectance data obtained from the sensors 50 can be transmitted to the control system 52 for storage and/or analysis, and associated information/data and alerts may be transmitted from the control system 52 to the graphic display 54.

As shown in FIG. 1, embodiments of the present invention may include one or more (e.g., a plurality) of sensors 50 for detecting portions of the EM spectrum that are reflected off crop material used to form bales. Such sensors 50 may be located on the tractor 12 towing the baler 14 or on the baler 14 itself. In embodiments in which a sensor 50 is positioned on the tractor, the sensor 50 may be positioned on a front of the tractor and directed/aimed downward so as to be configured to obtain EM reflectance data off crop material cut and arranged within a windrow on the surface of the field in front of the tractor 12 and the baler 14. Such crop material will be formed into bales by the baler 14 once picked up by the pickup assembly 22.

Alternatively, or in addition, embodiments may provide for a sensor 50 to be positioned between the tractor 12 and the baler 14 (e.g., on the tow bar 20 connecting the baler 14 to the tractor 12 and in front of the baler 14 pickup assembly 22), such that the sensor 50 can obtain EM reflectance data from the crop material located within the windrow on the ground between the tractor 12 and the baler 14. Such crop material will be formed into bales by the baler 14 once picked up by the pickup assembly 22.

In further alternatives, or in addition, a sensor 50 may be positioned on the baler 14 such that the sensor 50 can obtain EM reflectance data from the crop material being formed into bales by the baler 14. For example, the sensor 50 may be positioned on, in, or adjacent to the baling chambers 28 (e.g., rearward/downstream of the pickup assembly 22, the pre-compression chamber 24, the stuffer assembly 26, and/or the plungers 30). As such, the sensor 50 may detect multi-spectral EM reflectance data of the crop material being formed into a bale within the baling chambers 28. As was noted previously, the baler 14 may be configured to simultaneously form two or more bales of crop material via two or more baling chambers 28. Such embodiments of the present invention may include at least two sensors 50, with one of such sensors positioned on or within each baling chamber 28 of the baler 14. As such, the sensors 50 will be configured to obtain EM reflectance data/information for crop material being formed into bales in each of the baling chambers 28 (e.g., within each of the two baling chambers 28).

In even further alternatives, or in addition, a sensor 50 may be positioned on a rear portion of the baler 14 to obtain EM reflectance data from the bales of crop material after they are formed by the baler 14. As such, the sensor 50 may detect multi-spectral EM reflectance data of the crop material within the bales formed and ejected from the baling chambers 28 of the baler 14. The EM reflectance data may be obtained as the formed bales exiting the baler or once the bales have been deposited onto the surface of the field. In some embodiments, the system 10 may include a plurality of sensors positioned at each of the locations discussed above (and illustrated in FIG. 1).

Once the multi-spectral EM reflectance data is obtained by the sensors 50, such data can be transmitted to the control system 52 for analysis and processing. Specifically, at the control system 52, the multi-spectrum EM reflectance data can be converted into a vegetation index that can be used to determine the quality of crop material being formed into bales by the baler 14. For instance, a normalized difference vegetation index (NDVI) and a normalized difference red edge index (NDRE) are two vegetation indices that may be generated by the control system 52 from the EM reflectance data.

NDVI may be defined as:

$$NDVI = \frac{(NIR - \text{Red})}{(NIR + \text{Red})}$$

where "NIR" is the spectral reflectance measurement/data (e.g., intensity) obtained by the sensors 50 in the near-infrared region of the EM spectrum (e.g., between 750 and 2500 nm), and "Red" is the is the spectral reflectance measurement/data (e.g., intensity) obtained by the sensors 50 in the red (visible) region of the EM spectrum (e.g., between 625 and 740 nm).

NDRE may be defined as:

$$NDRE = \frac{(NIR - RE)}{(NIR + RE)}$$

where "NIR" is the spectral reflectance measurement/data (e.g., intensity) obtained by the sensors 50 in the near-infrared region of the EM spectrum (e.g., between 750 and 2500 nm), and RE is the is the spectral reflectance measurement/data (e.g., intensity) in the red edge region of the spectrum (e.g., between 680 to 730 nm, and centered around 715 nm).

Vegetation indexes have been used in the past to determine plant nitrogen needs and spot spraying of herbicides for crop growing in a field. However, vegetation indexes have not been utilized as a quality indicator for crop material after it has been cut, such as after crop material has been cut, arranged into windrows, collected, and formed into bales by a baler (e.g., baler 14). Although NDVI and NDRE are discussed above, it should be understood that embodiments of the present invention contemplate the use of other vegetation indices, such as the enhanced vegetation index (EVI).

Embodiments of the present invention may provide for the control system 52 to receive the EM reflectance data, e.g., in the form of RGB data values (e.g., intensities), infrared data values (e.g., intensities), red edge data values (e.g., intensities), or other spectrum data (e.g., intensities) obtained by the sensor 50 and to process such data to convert such data into vegetation index values (NDVI, NDVE, etc.). As was described previously, the control system 52 may be coupled and/or associated with the baler 14 or the tractor 12. As such, the analysis and/or processing of the EM reflectance data (or other information/data) may be performed by the control system 52 locally at the baler 14 or tractor 12. Alternatively, the control system 52 may be separated from the baler 14 and/or tractor 12, such that the analysis and/or processing of the EM reflectance data (or other information/data) may be performed by the control system 52 remotely from the baler 14 or tractor 12 (e.g., in the cloud).

The EM reflectance data and/or vegetation index values can be recorded for each bale formed by the baler or for groups of bales formed by the baler 14. The recorded EM reflectance data and/or vegetation index values may be associated with an individual bale or group of bales with a physical marker applied to the bale (e.g., a radio-frequency identification "RFID" tag that can be attached to the bale). In some embodiments, the baler 14 may be configured to generate the RFID tag and apply such tag to each bale. In more detail, the control system 52 may generate and store a data file for each bale or group of bales formed by the baler 14, with such data file including information associated with the respective bale or groups of bales. In some embodiments, the data files will include the EM reflectance data received by and/or vegetation index values calculated by the control system 52 for each bale or group of bales formed by the baler 14. As will be described in more detail below, other data, information, and/or parameters associated with each bale or groups of bales may also be included within the respective data files. Nevertheless, the RFID tags generated and placed on each bale or group of bales can be associated with a given data file for the bale or group of bales, such that the RFID tag can provide information (e.g., EM reflectance data and/or a vegetation index value) for the respective bale or group of bales. Beneficially, because the RFID tags are attached to the individual bales or groups of bales, such RFID tags can provide relevant information regarding the bales or groups of bales even if the bales or groups of bales are picked up and moved.

The EM reflectance data and/or vegetation index values may also be stored in a database (e.g., made available via the memory elements 58 associated with the control system 52) for future analysis and reference. As was described previously, such data storage may be integrated locally with the baler and/or tractor, or may be located remotely (e.g., in the cloud). In some embodiments, other data may be provided to the control system 52 recorded in conjunction with the EM reflectance data and/or vegetation index values as part of the data file for each bale or group of bales, such as location data (e.g., as perhaps obtained by a secondary sensors 50 in the form of global-positioning system "GPS" sensors associated with the tractor 12 or baler 14). As such, a geographic location of the bales may also be associated with the EM reflectance data and/or vegetation index values of such bales via the data files. In embodiments in which RFID tags are used, the RFID tags can associate the respective bales or groups of bales with EM reflectance data and/or vegetation index values and geographic location of the bales or groups of bales.

Embodiments of the present embodiments may also provide for the EM reflectance data and/or vegetation index values to be combined with other bale parameters, such as size, weight, pressure, moisture content, etc. The bale size (e.g., length, width, and/or thickness) may be obtained by secondary sensors 50 in the form of dimension measuring sensors, such as laser sensors, string potentiometers, etc. The bale weight may be measured by secondary sensors 50 in the form of weight measuring sensors, such as scales. The bale moisture may be measured by secondary sensors 50 in the form of water measuring sensors, such as volumetric sensors, tensiometers, electrical conductivity sensors, etc. Such bale parameters may be used, perhaps in conjunction with the vegetation indexes, to provide a comprehensive metric indicating bale quality. In some additional embodiments, the system 10 may include secondary sensors 50 in the form of load or pressure sensors configured to measure pressures at which the bales are formed. For instance, such pressure sensors may be associated with the baler 14 and configured to measure the pressure or loads imparted on the bales by the plungers 30 during compression cycles as the bales are formed in the baling chambers 28. Such bale parameters may be associated, e.g., in addition to the EM reflectance data, the vegetation index values, and/or the geographic location, of each bale or group of bales via the data files for each bale or group of bales. In embodiments in which RFID tags are used, the RFID tags can associate the respective bales or groups of bales with EM reflectance data, vegetation index values, bale parameters, and/or geographic location of the bales or groups of bales.

In view of the above, bale quality metrics for one or more bales may be obtained by using the sensors 50 to obtain multi-spectral EM reflectance data for (i) crop material that is to be formed into bales by the baler 14, and/or (ii) bales being formed or have been formed by the baler 14. From the EM reflectance data obtained by the sensors 50, one or more vegetation index values can be calculated and associated with the bale and/or group of bales from which the EM reflectance data was obtained. Embodiments provide for the vegetation index values to be stored by the control system 52 for future analysis and/or reference. As was described above, the control system 52 may store such vegetation index values locally (e.g., when the control system 52 is coupled and/or associated with the baler 14 or tractor 12) or remotely such as in the cloud (e.g., when the control system 52 is coupled and/or associated with the baler 14 or tractor 12). In some embodiments, the vegetation index values will be or will be converted to bale quality metrics, which can be associated with individual bales or groups of bales and stored in the control system 52. Regardless, embodiments provide for the EM reflectance data, the vegetation index values, and/or the bale quality metrics to be stored by the control system 52 for future analysis and/or reference. As was described above, the control system 52 may store such quality metrics locally (e.g., when the control system 52 is coupled and/or associated with the baler 14 or tractor 12) or remotely such as in the cloud (e.g., when the control system 52 is coupled and/or associated with the baler 14 or tractor 12).

In alternative embodiments, bale quality metrics for one or more bales may be obtained by using the sensors 50 to obtain multi-spectral EM reflectance data for (i) crop material that is to be formed into bales by the baler 14, and/or (ii) bales being formed or have been formed by the baler 14. From the EM reflectance data, one or more vegetation index values can be calculated and associated with the bale and/or group of bales from which the EM reflectance data was obtained. Furthermore, other bale parameters (e.g., size, weight, moisture, pressure, etc.) may also be determined and associated with the bale and/or group of bales from which the EM reflectance data was obtained. Embodiments provide for the vegetation index values and other bale parameters to be stored by the control system 52 for future analysis and/or reference. As was described above, the control system 52 may store such vegetation index values and/or other bale parameters locally (e.g., when the control system 52 is coupled and/or associated with the baler 14 or tractor 12) or remotely such as in the cloud (e.g., when the control system 52 is coupled and/or associated with the baler 14 or tractor 12). In some embodiments, the vegetation index values will be combined with the other bale parameters to generate bale quality metrics, which are associated with individual bales or groups of bales and stored in the control system 50. Regardless, embodiments provide for the EM reflectance data, the vegetation index values, the other bale parameters, and/or the bale quality metrics to be stored by the control system 52 for future analysis and/or reference. As was described above, the control system 52 may store such quality metrics locally (e.g., when the control system 52 is coupled and/or associated with the baler 14 or tractor 12) or remotely such as in the cloud (e.g., when the control system 52 is coupled and/or associated with the baler 14 or tractor 12).

In certain embodiments, the system 10 may include a graphic display 54 for presenting information to an operator of the baler 14 relevant to the composition of the bale. The graphic display 54 may be generally equivalent to the graphic display 44 described previously. As such, the EM reflectance data, the vegetation index values, the other bale parameters, and/or the bale quality metrics of the bales being formed by the baler 14 may be transmitted from the control system 52 to the graphic display 54 to present such information to the operator of the baler 14 in near real-time. The graphic display 54 may be positioned in the cab of the tractor 12 such that the operator can readily observe the information presented thereon. In some embodiments, each of the physical RFID tags generated and positioned on the bales may include or otherwise be associated with the EM reflectance data, the vegetation index values, the other bale parameters, and/or the bale quality metrics of the bale to which the RFID is attached.

In some embodiments, one or more target data/values/metrics may be programmed (e.g., via the control system 52 and/or graphic display 54), such that if any of the EM reflectance data, the vegetation index values, the other bale parameters, and/or the bale quality metrics are out of range of target data/values/metrics (e.g., exceed or fall below target data/values/metrics), the graphic display 54 may present an alert (visible and/or audible) so as to alert the operator of the baler 14 that a bale quality issue exists. Stated differently, the graphic display 54 may present an alert when (i) the EM reflectance data obtained by the image sensors 50 is out of range of a target EM reflectance data, (ii) the vegetation index values generated by the control system 52 are out of range of a target vegetation index values, (iii) the bale parameters obtained by the secondary sensors 50 are out of range of a target bale parameters. and/or (iv) the bale quality metrics generated by the control system 52 are out of range of a target bale quality metric. As such, the operator can temporarily halt operations to correct the bale quality issue in near real-time. In some other embodiments, the system 10 may transmit an alert to a remote location, such as to a remote computing device (e.g., a mobile device of the operator).

In some embodiments, the control system 52 may also be configured to determine if a bale was actively being formed (e.g., such a via sensors associated with the baler 14 and configured to determine if a bale was being formed and/or was passing through the baler 14) so that EM reflectance data obtained when the bale was not being formed (for example when the baler 14 turning around at the end of a row) would not be recorded by the control system 52.

Returning to the control system 52, as was described above, the control system 52 may receive the EM reflectance data from the sensors 50, as well as other bale parameters from secondary sensors 52. The control system 52 may process the EM reflectance data to generate vegetation index values and/or bale quality metrics. In embodiments in which the control system 52 is connected to and/or otherwise associated with the baler 14 and/or tractor 12, such processing may be performed locally at the baler 14 and/or tractor 12. In embodiments in which the control system 52 is remotely located from the baler 14 and/or tractor 12, such processing may be performed remotely from the baler and/or tractor 12 (e.g., in the cloud). In some embodiments, the control system 52 will generate a data file for each bale or group of bales formed by the baler 14. Each data file may include the EM reflectance data, vegetation index value, geographic location, bale parameters, and/or quality metrics for the respective bale or group of bales. Such data files may be stored on the control system 52 for future use, analysis, and/or processing. In embodiments in which the control system 52 is connected to and/or otherwise associated with the baler 14 and/or tractor 12, the data files may be stored locally at the baler and/or tractor 12. In embodiments in which the control system 52 is remotely located from the baler 14 and/or tractor 12, the data files may be stored remotely from the baler 14 and/or tractor 12 (e.g., in the cloud). In still other embodiments, a portion of the control system 52 may be located locally at the baler 14 and/or tractor 12, while a portion may be located remotely. As such, the processing and data storage of the control system 52 may be performed locally and/or remotely.

In embodiments in which an RFID tag is generated and attached to each bale or groups of bales, each RFID tag may be associated with the data file for the respective bale or groups of bales (with such data files being stored in the control system 52). As such, the RFID tag may provide a user with various information related to the bale or group of bales, such as EM reflectance data, vegetation index values, bale parameters (e.g., bale size, weight, moisture content, bale pressure, etc.), geographic location (e.g., where the bale was formed and deposited by the baler 14), and/or quality metrics. Because the RFID tags would remain attached to the bale or group of bales, such information may be accessed even if the bale or group of bales are moved from their original location. In other embodiments, RFID tags may not be used. Nevertheless, for each bale or groups of bales, a data file may be created and stored in the control system 52. Such data files can be accessed to provide a user with various information related to the bale or group of bales, such as EM reflectance data, vegetation index values, bale parameters (e.g., bale size, weight, moisture content, bale pressure, etc.), geographic location (e.g., where the bale was formed and deposited by the baler 14), and/or quality metrics.

In view of the above, embodiments of the present invention include a method for determining bale quality and/or composition of one or more bales being formed by a baler 14. The method may include a step of picking up crop material cut and laying on the ground in the form of a windrow. An additional step includes forming the crop material into bales. An additional step includes obtaining electromagnetic reflectance information for the crop material. A further step includes generating vegetation index values for the bales of crop material based on the electromagnetic reflectance information.

Although the steps of the methods and/or process described herein may be described or claimed in a particular sequential order, such processes may be configured to work in different orders. In other words, any sequence or order of steps that may be explicitly described or claimed does not necessarily indicate a requirement that the steps be performed in that order. The steps of methods or processes described herein may be performed in any order possible. Further, some steps may be performed simultaneously despite being described or implied as occurring non-simultaneously (e.g., because one step is described after the other step). For example, in the method described above for determining bale quality and/or composition of one or more bales, the electromagnetic reflectance information for the crop material may be obtained (e.g., via the variously placed sensors 50) prior to, during, and/or after the crop material has been picked up and/or formed into bales.

Although the invention has been described with reference to the one or more embodiments illustrated in the figures, it is understood that equivalents may be employed and substitutions made herein without departing from the scope of the invention as recited in the claims.

Having thus described one or more embodiments of the invention, what is claimed as new and desired to be protected by Letters Patent includes the following:

1. A bale composition determination system comprising:
   a baler configured to pick up crop material cut and lying on the ground in the form of a windrow and to form bales of the crop material;
   one or more primary sensors configured to obtain electromagnetic reflectance information for the crop material; and
   a control system configured to receive the electromagnetic reflectance information for the crop material and to generate vegetation index values for the bales of crop material based on the electromagnetic reflectance information,
   further comprising one or more secondary sensors configured to obtain bale parameters for the bales of crop material, wherein the bale parameters include one or more of the following: size, weight, and moisture content for the bales,
   wherein the control system is configured to generate bale quality metrics for the bales, wherein the bale quality metrics are based on the vegetation index values and the bale parameters,
   further comprising a graphic display configured to present an alert when the bale quality metric is out of range of a target.

2. The bale composition determination system of claim 1, wherein said baler is a small, square baler configured to form small, square bales of crop material.

3. The bale composition determination system of claim 1, wherein said baler is pulled by a tractor.

4. The bale composition determination system of claim 3, wherein said primary sensor is positioned on the tractor and is configured to obtain electromagnetic reflectance information for the cut crop material lying on the ground in the windrow.

5. The bale composition determination system of claim 3, wherein said primary sensor is positioned on a towbar extending between said baler and the tractor and is configured to obtain electromagnetic reflectance information for the cut crop material lying on the ground in the windrow.

6. The bale composition determination system of claim 1, wherein said primary sensor is positioned on or within a baling chamber of said baler, and wherein said primary sensor is configured to obtain electromagnetic reflectance information for crop material being formed into a bale within the baling chamber.

7. The bale composition determination system of claim 1, wherein said primary sensor is positioned on a back side of said baler, and wherein said primary sensor is configured to obtain electromagnetic reflectance information for crop material having been formed into a bale and that is ejected from said baler.

8. The bale composition determination system of claim 1, wherein said primary sensor comprises a multi-spectral image sensor.

9. The bale composition determination system of claim 8, wherein said multi-spectral image sensor is configured to obtain red-green-blue reflectance information for the crop material.

10. The bale composition determination system of claim 1, wherein vegetation index values comprise normalized difference vegetation index values.

11. A bale composition determination system comprising:
    a baler configured to pick up crop material cut and lying on the ground in the form of a windrow and to form bales of the crop material;
    one or more primary sensors configured to obtain electromagnetic reflectance information for the crop material; and
    a control system configured to receive the electromagnetic reflectance information for the crop material and to generate vegetation index values for the bales of crop material based on the electromagnetic reflectance information,
    further comprising one or more secondary sensors configured to obtain bale parameters for the bales of crop material, wherein the bale parameters include one or more of the following: size, weight, and moisture content for the bales,
    wherein the control system is configured to generate bale quality metrics for the bales, wherein the bale quality metrics are based on the vegetation index values and the bale parameters,
    wherein said baler is configured to generate a radio-frequency identification tag to be placed on each bale, wherein each radio-frequency identification tag includes or is associated with information indicative of a bale quality metric for the respective bale.

12. The bale composition determination system of claim 1, wherein said control system is positioned remotely from said baler, and wherein the vegetation index values are generated by said control system via said control system processing the electromagnetic reflectance information remotely from said baler.

13. The bale composition determination system of claim 12, wherein said control system stores the electromagnetic reflectance information or vegetation index values remotely from said baler.

14. A bale composition determination system for bales of crop material formed by a baler, wherein the baler is configured to pick up the crop material having been cut and lying on the ground in the form of a windrow, said system comprising:
    one or more sensor configured to obtain electromagnetic reflectance information for the crop material; and
    a computing device configured to receive the electromagnetic reflectance information for the crop material and to generate vegetation index values for the bales of crop material based on the electromagnetic reflectance information, wherein said control system is configured to generate a data file for each bale or group of bales formed by said baler, wherein said data files include electromagnetic reflectance information or vegetation index values for each bale or group of bales.

15. The bale composition determination system of claim 14, wherein the data files additionally include a geographic location, a size, a weight, and/or a moisture content for each bale or group of bales formed by said baler.

16. The bale composition determination system of claim 14, wherein said control system is positioned remotely from said baler, and wherein the data files are stored remotely from said baler.

17. The bale composition determination system of claim 14, wherein said control system is positioned on or in said baler.

18. The bale composition determination system of claim 14, wherein said control system is positioned on or in a tractor configured to propel said baler.

19. A method for determining bale composition, said method comprising the steps of:
 (a) picking up crop material cut and lying on the ground in the form of a windrow;
 (b) forming the crop material into bales;
 (c) obtaining electromagnetic reflectance information for the crop material; and
 (d) generating vegetation index values for the bales of crop material based on the electromagnetic reflectance information,
 further including the step of providing an alert that the vegetation index values generated in step (d) are out of range of target vegetation index values.

20. The method of claim 19, wherein said picking up and forming of steps (a) and (b) are performed by a small, square baler configured to form small, square bales of crop material.

21. The method of claim 19, wherein said obtaining of step (c) includes a multi-spectral image sensor obtaining red-green-blue reflectance information for the crop material.

22. The method of claim 19, wherein the vegetation index values generated in step (d) comprise normalized difference vegetation index values.

23. The method of claim 19, wherein said obtaining of step (c) is performed after said picking up and forming of steps (a) and (b).

24. The method of claim 19, wherein said obtaining of step (c) is performed prior to said picking up and forming of steps (a) and (b).

* * * * *